(12) United States Patent
Zhang et al.

(10) Patent No.: US 10,494,680 B2
(45) Date of Patent: Dec. 3, 2019

(54) **PRIMER PAIR, KIT AND METHOD FOR DETECTING *BABESIA GIBSONI***

(71) Applicant: Delta Electronics Int'l (Singapore) Pte Ltd, Singapore (SG)

(72) Inventors: Yong Zhang, Singapore (SG); Chih-Yu Chao, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 24 days.

(21) Appl. No.: 15/683,987

(22) Filed: Aug. 23, 2017

(65) Prior Publication Data

US 2019/0055611 A1    Feb. 21, 2019

(30) Foreign Application Priority Data

Aug. 15, 2017  (SG) .......................... 10201706663R

(51) Int. Cl.
| | |
|---|---|
| *C12Q 1/68* | (2018.01) |
| *C07H 21/04* | (2006.01) |
| *C12Q 1/6893* | (2018.01) |
| *C12Q 1/686* | (2018.01) |
| *C12Q 1/6888* | (2018.01) |

(52) U.S. Cl.
CPC .......... *C12Q 1/6893* (2013.01); *C12Q 1/686* (2013.01); *C12Q 1/6888* (2013.01)

(58) Field of Classification Search
None
See application file for complete search history.

(56) References Cited

FOREIGN PATENT DOCUMENTS

| | | |
|---|---|---|
| CN | 102230008 | 3/2013 |
| CN | 103103286 | 10/2014 |
| CN | 104293903 | 1/2015 |
| CN | 102558332 | 7/2017 |

OTHER PUBLICATIONS

NEB catalog (1998/1999), pp. 121, 284. (Year: 1998).*
Mandal et al. (Infection, Genetics, and Evolution, vol. 27, pp. 325-331, 2014 (Year: 2014).*
Wang et al. (Veterinary Parasitology, vol. 168, pp. 11-18, 2010) (Year: 2010).*
Liu, et al., Babesia gibsoni internal transcribed spacer 1 region is highly conserved amongst isolates from dogs across Japan; Parasitology, Published Jan. 22, 2016, p. 863-865.
Mandal, et al., Genetic characterization and phylogenetic relationships based on 18S rRNA and ITS1 region of small form of canine *Babesia* spp. from India; Infection, Genetics and Evoluation, Published Aug. 10, 2014, p. 325-331.
NCBI GenBank KT033509.1, Babesia gibsoni isolate Fukuoka 39 internal transcribed spacer 1, partial sequence; Published Jun. 16, 2016, p. 1.
Youn-Kyoung Goo et al., "New Molecules in Babesia gibsoni and Their Application for Diagnosis, Vaccine Development, and Drug Discovery". Korean J Parasitol vol. 52, No. 4: 345-353; Aug. 2014.

* cited by examiner

*Primary Examiner* — Jeanine A Goldberg
(74) *Attorney, Agent, or Firm* — Kirton McConkie; Evan R. Witt

(57) ABSTRACT

Primer pair, kit and method for detecting *Babesia gibsoni* are disclosed. The primer pair includes a forward primer and a reverse primer, and the kit includes the primer pair and a probe. The forward primer has a sequence of SEQ ID NO: 1, the reverse primer has a sequence of SEQ ID NO: 2, and the probe has a sequence of SEQ ID NO: 3.

4 Claims, 4 Drawing Sheets

Specification includes a Sequence Listing.

| Name | Sequence |
|---|---|
| Forward Primer | 5'- TTGAAACTTGTCGAGCTG -3'   (SEQ ID NO: 1) |
| Reverse Primer | 5'- TGGAATCTTCCACGACTG -3'   (SEQ ID NO: 2) |
| Probe | 5'- CCGAGGCAACACGCGATC -3'   (SEQ ID NO: 3) |

FIG. 2

PRIMER PAIR, KIT AND METHOD FOR DETECTING *BABESIA GIBSONI*

CROSS-REFERENCE TO RELATED APPLICATION

This application claims the priority to Singapore Patent Application No. 10201706663R filed on Aug. 15, 2017, the entire contents of which are incorporated herein by reference for all purposes.

FIELD OF THE INVENTION

The present invention relates to primer pair, kit and method for detecting *Babesia* species, and more particularly to primer pair, kit and method for detecting *Babesia gibsoni*.

BACKGROUND OF THE INVENTION

Various kinds of *Babesia* species can infect dogs, and the most common ones are *Babesia canis* (also called large *Babesia*) and *Babesia gibsoni* (also called small *Babesia*). *Babesia gibsoni* is mainly distributed in Asia, including Japan, Korea, Taiwan and Malaysia. It is now also recognized as being widely distributed in Africa, Middle East, Brazil, North America, and Australia. *Babesia gibsoni* is an intraerythrocytic apicomplexan parasite that causes piroplasmosis in dogs. This disease is mainly transmitted naturally by ticks, but many reports have demonstrated transmission by dog bites and blood transfusions and transmission via the route to the developing fetus. *Babesia gibsoni* infection occurs frequently in dogs, and recently has become a serious problem from a clinical viewpoint, because the acute form of the disease typically results in serious clinical problems, such as fever, thrombocytopenia, regenerative anemia, splenomegaly, and sometimes death. Furthermore, infected animals may become chronic carriers and transmit the disease via ticks to other animals. Therefore, in order to control *Babesia gibsoni* infection, rapid and accurate diagnosis followed by prompt effective treatment, and the prevention of chronic carriers are needed.

Since the therapeutic approaches for *Babesia canis* and *Babesia gibsoni* are different, it is important to rapidly and correctly diagnose *Babesia gibsoni* to avoid inadequate treatment. However, *Babesia gibsoni* is not easy to be diagnosed. Generally, the methods employed for *Babesia gibsoni* diagnosis include blood smear, serologic diagnosis and molecular diagnosis, but each method has some limitations.

A veterinarian may perform direct pathogen detection in blood smears stained by Giemsa, but it is hard to differentiate large and small *Babesia* species in stained blood smears. This method significantly depends for its accuracy on well-trained and experienced technologists. Besides, this method requires fresh samples to preserve organism viability and morphology, and thus the samples must be processed very quickly.

Serologic diagnosis may be helpful in identifying the presence of antibodies to *Babesia gibsoni*, but serology cannot distinguish between animals with an acute or chronic infection. The limitations of serologic diagnosis are cross-reactions (especially between different *Babesia* species), which results in reduced specificity, and false-negative findings in young or immunosuppressed dogs, or early in the course of infection before seroconversion has occurred.

One of the current and workable way to diagnose *Babesia gibsoni* is molecular diagnosis, especially by polymerase chain reaction (PCR) testing. PCR, which is more sensitive and specific technique, offers an alternative approach for the diagnosis of babesiosis. An 18S rRNA gene sequence has been helpful in identifying species of *Babesia* and related protozoa. For example, the canine babesiosis 18S ribosomal RNA (18S) gene genesig standard kit provided by Primerdesign Ltd. is used to diagnose canine babesiosis. However, this kit cannot differentiate *Babesia canis* (large *Babesia*) and *Babesia gibsoni* (small *Babesia*).

Thus, there is a need of providing a method of specifically detecting *Babesia gibsoni* in order to select an appropriate treatment.

SUMMARY OF THE INVENTION

An object of the embodiment of the present invention is to provide a primer pair for detecting *Babesia gibsoni* with high sensitivity and high specificity in order to rapidly and correctly diagnose *Babesia gibsoni* infection and select an appropriate treatment.

An another object of the embodiment of the present invention is to provide a kit for detecting *Babesia gibsoni* with high sensitivity and high specificity in order to rapidly and correctly diagnose *Babesia gibsoni* infection and select an appropriate treatment.

An additional object of the embodiment of the present invention is to provide a method for detecting *Babesia gibsoni* with high sensitivity and high specificity in order to rapidly and correctly diagnose *Babesia gibsoni* infection and select an appropriate treatment.

According to an aspect of the embodiment of the present invention, there is provided a primer pair for detecting *Babesia gibsoni*, including a forward primer or the complementary sequence thereof, wherein the forward primer includes a sequence of 5'-TTGAAACTTGTCGAGCTG-3' (SEQ ID NO: 1); and a reverse primer or the complementary sequence thereof, wherein the reverse primer includes a sequence of 5'-TGGAATCTTCCACGACTG-3' (SEQ ID NO: 2).

According to an aspect of the embodiment of the present invention, the forward primer and the reverse primer are used for real-time polymerase chain reaction.

According to another aspect of the embodiment of the present invention, there is provided a kit for detecting *Babesia gibsoni*, including a forward primer or the complementary sequence thereof, wherein the forward primer includes a sequence of 5'-TTGAAACTTGTCGAGCTG-3' (SEQ ID NO: 1); a reverse primer or the complementary sequence thereof, wherein the reverse primer includes a sequence of 5'-TGGAATCTTCCACGACTG-3' (SEQ ID NO: 2); and a probe.

In an embodiment of the present invention, the probe includes a sequence of 5'-CCGAGGCAACACGCGATC-3' (SEQ ID NO: 3).

In an embodiment of the present invention, the forward primer, the reverse primer, and the probe are used for real-time polymerase chain reaction.

In an embodiment of the present invention, the probe is labeled with a 5'-reporter dye and a 3'-quencher.

According to an additional aspect of the embodiment of the present invention, there is provided a method for detecting *Babesia gibsoni*, wherein the method includes amplifying nucleic acid from *Babesia gibsoni* using real-time polymerase chain reaction with a forward primer or the complementary sequence thereof, a reverse primer or the complementary sequence thereof, and a probe, wherein the forward primer includes a sequence of 5'-TTGAAACTT- GTCGAGCTG-3' (SEQ ID NO: 1), and the reverse primer includes a sequence of 5'-TGGAATCTTCCACGACTG-3' (SEQ ID NO: 2).

In an embodiment, the probe includes a sequence of 5'-CCGAGGCAACACGCGATC-3' (SEQ ID NO: 3). The probe is labeled with a 5'-reporter dye and a 3'-quencher.

The above objects and advantages of the embodiments of the present invention become more readily apparent to those ordinarily skilled in the art after reviewing the following detailed description and accompanying drawings, in which:

BRIEF DESCRIPTION OF THE DRAWINGS

FIG. 2 shows the DNA sequences of the forward primer, the reverse primer, and the probe.

DETAILED DESCRIPTION OF THE PREFERRED EMBODIMENT

The present invention will now be described more specifically with reference to the following embodiments. It is to be noted that the following descriptions of the embodiments of this invention are presented herein for purpose of illustration and description only; it is not intended to be exhaustive or to be limited to the precise form disclosed.

The embodiment of the present invention utilizes real-time polymerase chain reaction (Real-time PCR), also called quantitative polymerase chain reaction (Q-PCR), with probe-based detection for detecting Babesia gibsoni. In Real-time PCR, the specific forward and reverse primers and probe hybridize to the DNA target of Babesia gibsoni, wherein the probe is labeled with a 5'-reporter dye and a 3'-quencher. During PCR amplification, the probe is cleaved, and the reporter dye and quencher are separated, so that the resulting increase in fluorescence may be detected. In an embodiment, the reporter dye is FAM fluorescence, and the quencher is BHQ1 group.

Figure 1:
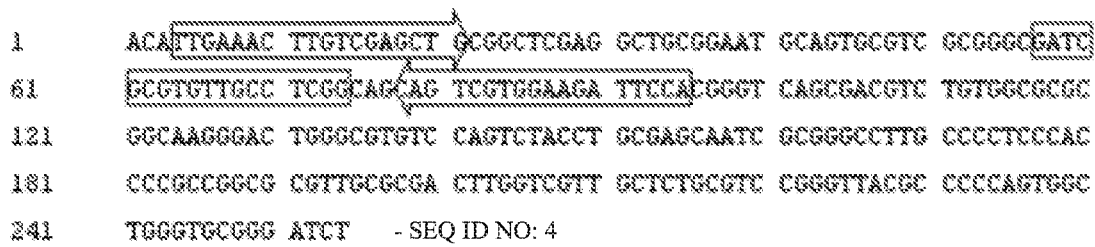
FIG. 1 shows the corresponding positions of the forward primer, the reverse primer, and the probe on the sequence of the ITS1 gene.

The DNA target for this assay is a variable region of the Internal Transcribed Spacer 1 (ITS1, GenBank accession number: KT033509.1) including sequence which is species-specific for Babesia gibsoni. PCR primers and probe are designed by Primer3 and chosen on the basis of GC content and lack of hairpin structures. FIG. 1 shows the corresponding positions of the forward primer, the reverse primer, and the probe on the sequence of the ITS1 gene (SEQ ID NO: 4). As shown in FIG. 1, the forward primer starts at position 4, the probe starts at position 74, and the reverse primer starts at position 95. The primers and probe combination is predicted to amplify the DNA of Babesia gibsoni strains with an amplicon size of 92-bp. FIG. 2 shows the DNA sequences of the forward primer, the reverse primer, and the probe, wherein the forward primer (SEQ ID NO: 1) includes 18-mer, the reverse primer (SEQ ID NO: 2) includes 18-mer, and the probe (SEQ ID NO: 3) includes 18-mer.

To ascertain the specificity of the PCR primers and the probe for Babesia gibsoni, the primer pair, including the forward primer and the reverse primer, and the probe are checked by Primer-BLAST from NCBI, and the result shows that no other similar species have 100% same fragment compare to the primer pair and the probe of the embodiment of the present invention. The result demonstrates that the specificity of the primer pair and the probe is quite high, and the primer pair and the probe may be used to amplify and detect the ITS1 gene of Babesia gibsoni. In one embodiment of the present invention, the primer pair and the probe can be only used to amplify and detect the ITS1 gene of Babesia gibsoni.

Therefore, the embodiment of the present invention provides a primer pair for detecting Babesia gibsoni, including a forward primer or the complementary sequence thereof, and reverse primer or the complementary sequence thereof, wherein the forward primer includes a sequence of 5'-TTGAAACTTGTCGAGCTG-3' (SEQ ID NO: 1), and the reverse primer includes a sequence of 5'-TGGAATCTTCCACGACTG-3' (SEQ ID NO: 2). The embodiment of the present invention also provides a kit for detecting Babesia gibsoni, including a forward primer or the complementary sequence thereof, a reverse primer or the complementary sequence thereof, and a probe, wherein the forward primer includes a sequence of 5'-TTGAAACTTGTCGAGCTG-3' (SEQ ID NO: 1), and the reverse primer having a sequence of 5'-TGGAATCTTCCACGACTG-3' (SEQ ID NO: 2). In one embodiment, the probe includes a sequence of 5'-CCGAGGCAACACGCGATC-3' (SEQ ID NO: 3).

On the other hand, the embodiment of the present invention also provides a method for detecting Babesia gibsoni, wherein the method includes amplifying nucleic acid from Babesia gibsoni using real-time polymerase chain reaction with a forward primer, a reverse primer, and a probe, wherein the forward primer includes a sequence of 5'-TTGAAACTTGTCGAGCTG-3' (SEQ ID NO: 1), and the reverse primer includes a sequence of 5'-TGGAATCTTCCACGACTG-3' (SEQ ID NO: 2). In the method for detecting Babesia gibsoni of the embodiment, the probe includes a sequence of 5'-CCGAGGCAACACGCGATC-3' (SEQ ID NO: 3).

In some other embodiments, since the primer pair is specific to Babesia gibsoni, all the sequence located between the forward primer and the reverse primer may be used as the probe sequence, and thus, the probe sequence is not limited to the aforesaid sequence. Further, the probe may be designed to hybridize to any strand of the DNA, so both the complementary sequences at the same location may be used as the probe sequence. Therefore, the complementary sequence of the aforesaid probe sequence may also be used as the probe sequence for detecting Babesia gibsoni.

The following describes an example of the method for detecting Babesia gibsoni of the embodiment of the present invention.

First, DNA is extracted from 200 μl of EDTA-preserved whole blood using the QIAamp DNA blood Mini kit for blood protocol (from Qiagen) and eluted in 100 μl of elution buffer. Then the real-time PCR assay is performed on the Bio-Rad real-time PCR machine (CFX96). The PCR reaction mixture includes 10 μl of KAPA Fast probe universal master mix, 250 nM of forward and reverse primers and 250 nM of probe, wherein the forward primer has a sequence of 5'-TTGAAACTTGTCGAGCTG-3' (SEQ ID NO: 1), the reverse primer has a sequence of 5'-TGGAATCTTCCACGACTG-3' (SEQ ID NO: 2) and the probe has a sequence of 5'-CCGAGGCAACACGCGATC-3' (SEQ ID NO: 3). 3 μl extracted DNA template is added to each reaction in a total volume of 20 μl. Cycling conditions are as follows: 95° C. for 3 min, followed by 40 cycles of denaturation at 95° C. for 3 sec, and annealing/extension at 60° C. for 20 sec.

A Babesia gibsoni-positive control is constructed by cloning the 254-bp ITS1 gene fragment into a vector (PUC57 System). A series of seven 10-fold dilutions are prepared from this recombinant plasmid DNA (1.25×10, 1.25×10², 1.25×10³, 1.25×10⁴, 1.25×10⁵, 1.25×10⁶, 1.25×10⁷ copies/μl). The dilution series are analyzed in triplicate to determine the lower limit of *Babesia gibsoni* DNA detection and the linearity and efficiency of amplification of this real-time PCR assay.

Figure 3A:
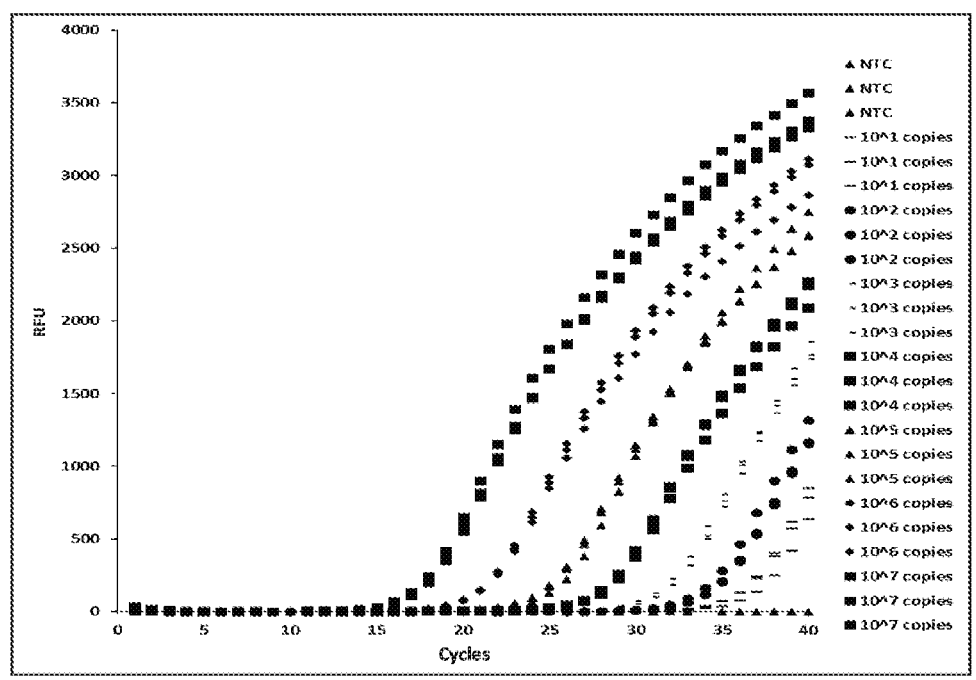
FIGS. 3A and 3B show the analysis of the amplification of the real-time PCR assay.
Figure 3B:
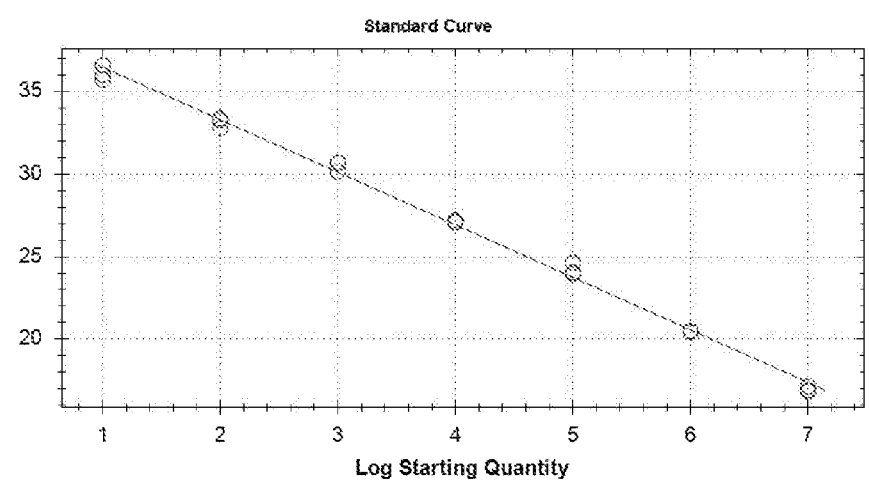

FIGS. 3A and 3B show the analysis of the amplification of the real-time PCR assay. FIG. 3A shows the amplification curve of different copies of plasmid samples, which reveals that the assay has high sensitivity. FIG. 3B show the assay has good linearity with an $R^2$ of 0.996, which is very close to the theoretical optimum of 1.0. Therefore, the assay may be expanded as a quantitative assay to estimate gene copy number and, by extension, percent parasitemia in clinical samples.

In conclusion, the embodiment of the present invention provides a method for detecting *Babesia gibsoni* using real-time PCR with specific primer pair and probe. The method of the embodiment of the present invention has advantage of high sensitivity, and can allow the detection of low parasitemia in subclinically infected cases. The method of the embodiment of the present invention further has advantage of high specificity, which is able to differentiate *Babesia* species, and this is important in order to select an appropriate treatment for *Babesia gibsoni*, as large *Babesia* and small *Babesia* require different therapeutic approaches. Further, compared to other *Babesia gibsoni* diagnosis methods, the method of the embodiment of the present invention is less time consuming and labor intensive, hence it is suitable for high throughput screening.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

---

What is claimed is:

1. A method for detecting *Babesia gibsoni*, the method comprising amplifying nucleic acid from *Babesia gibsoni* using real-time polymerase chain reaction with a forward primer, a reverse primer, and a probe, wherein the forward primer consists of a sequence of 5'-TTGAAACTTGTCGAGCTG-3' (SEQ ID NO: 1), and the reverse primer consists of a sequence of 5'-TGGAATCTTCCACGACTG-3' (SEQ ID NO: 2).

2. The method according to claim 1, wherein the probe consists of a sequence of 5'-CCGAGGCAACACGCGATC-3' (SEQ ID NO: 3).

3. The method according to claim 2, wherein the probe is labeled with a 5'-reporter dye and a 3'-quencher.

4. The method according to claim 1, wherein the probe is labeled with a 5'-reporter dye and a 3'-quencher.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 1
ttgaaacttg tcgagctg                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 2
tggaatcttc cacgactg                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetically generated probe

<400> SEQUENCE: 3
ccgaggcaac acgcgatc                                                 18

<210> SEQ ID NO 4
<211> LENGTH: 254
<212> TYPE: DNA
<213> ORGANISM: Babesia gibsoni

<400> SEQUENCE: 4
acattgaaac ttgtcgagct gcggctcgag gctgcggaat gcagtgcgtc gcgggcgatc      60
gcgtgttgcc tcggcagcag tcgtggaaga ttccacgggt cagcgacgtc tgtggcgcgc     120
ggcaagggac tgggcgtgtc cagtctacct gcgagcaatc gcgggccttg ccctcccac      180 cccgccggcg cgttgcgcga cttggtcgtt gctctgcgtc cgggttacgc ccccagtggc     240
tgggtgcggg atct                                                      254